United States Patent [19]

Chien

[11] Patent Number: 5,656,420
[45] Date of Patent: Aug. 12, 1997

[54] METHOD FOR EMPLOYING THE DELTA OPIOID DADLE TO EXTEND TISSUE SURVIVAL TIME DURING ISCHEMIA

[75] Inventor: Sufan Chien, Lexington, Ky.

[73] Assignee: University Of Kentucky Research Foundation, Lexington, Ky.

[21] Appl. No.: 393,642

[22] Filed: Feb. 24, 1995

[51] Int. Cl.$^6$ .................................................... A01N 1/02
[52] U.S. Cl. .................................................. 435/1.2; 424/75
[58] Field of Search ............................. 424/75; 435/1.2

[56] References Cited

PUBLICATIONS

Su et al., "Novel Actions of a Delta Opoid Peptide DADLE: From Hibernation to Organ Preservation", Society For Neuroscience Abstracts, 19(1–3) p. 421 (1993).
Wuethrich, B., "Organs Last Longer with Opiates", New Scientist, vol. 140, No. 1902, p. 20, Published Dec. 1993.
Chien et al., "Extension of Tissue Survival Time in Multiorgan Block Preparation with a Delta Opoid DADLE", The Journal of Thoracic and Cardiovascular Surgery, 107(3), pp. 964–967, Mar. 1994.

*Hibernation Induction Trigger for Organ Preservation*, Chapter 5, pp. 88–104, Extending Organ Survival Time Using Delta Opioid (DADLE), Sufan Chien, MD. Peter R. Oeltgen, Ph.D.
*Life Sciences*, vol. 46, pp. 1279–1286, Sigma And Opioid Receptors In Human Brain Tumors, Gail E. Thomas et al.
*The Journal of Thoracic and Cardiovascular Surgery*, vol. 103, No. 6, Jun., 1992, pp. 1136–1142, Reliable eighteen–hour lung preservation at 4° and 10°C by pulmonary artery flush after high–dose prostaglandin $E_1$ administration, Eckhard Mayer, MD et al.
*The Journal of Thoracic and Cardiovascular Surgery*, vol. 95, No. 1, Jan., 1988, pp. 55–61, A simple technique for multiorgan preservation, Sufan Chien, MD et al.

*Primary Examiner*—Frederick Krass
*Attorney, Agent, or Firm*—Lowe, Price, LeBlanc & Becker

[57] ABSTRACT

This invention concerns a method for extending the survival time of mammalian lung tissue subjected to ischemia, by which said tissue is perfused with a preservation solution comprising a therapeutic dose of the delta opioid DADLE ([D-Ala$^2$,D-Leu$^5$]-Enkephalin) under hypothermic conditions.

9 Claims, 5 Drawing Sheets

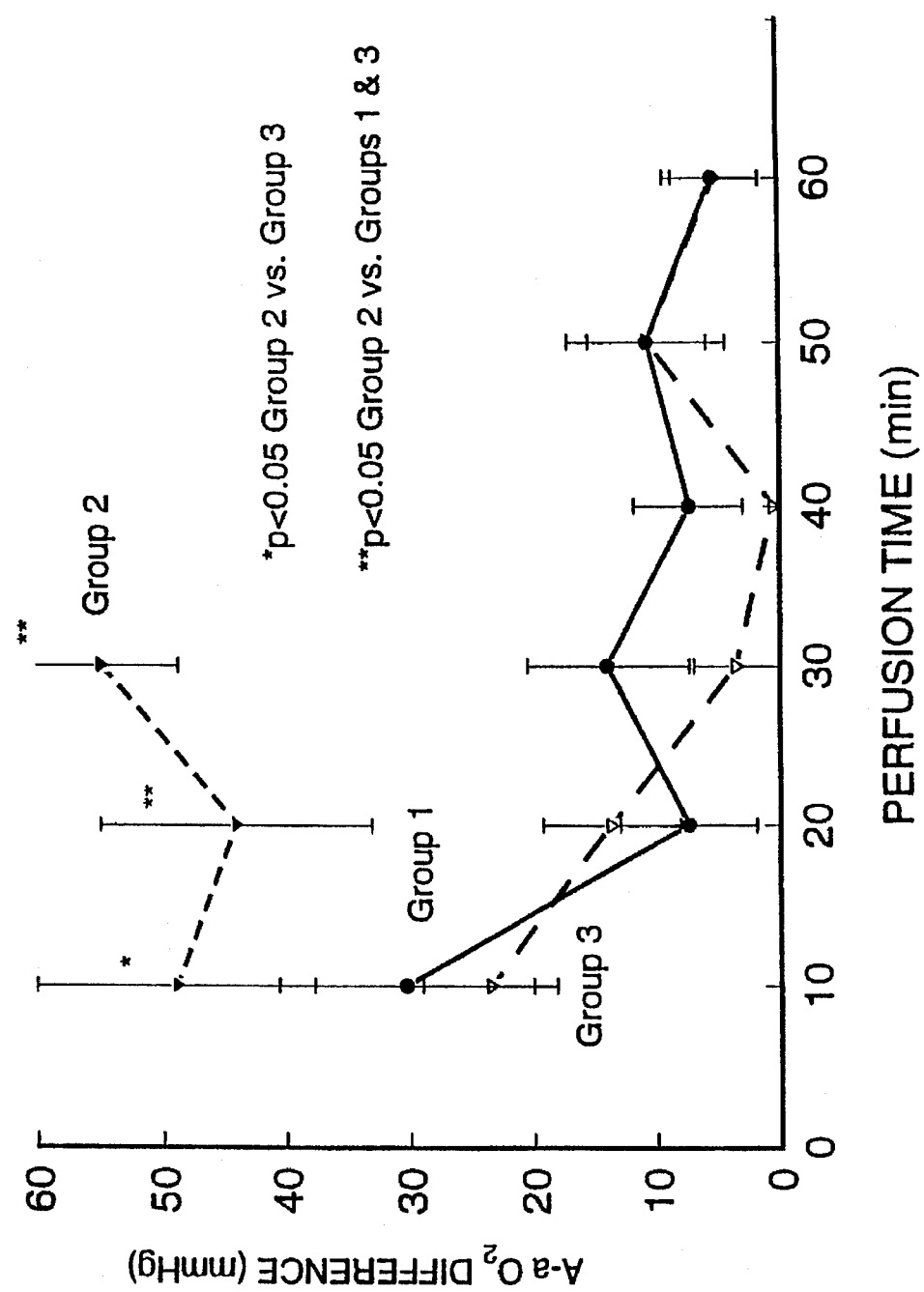

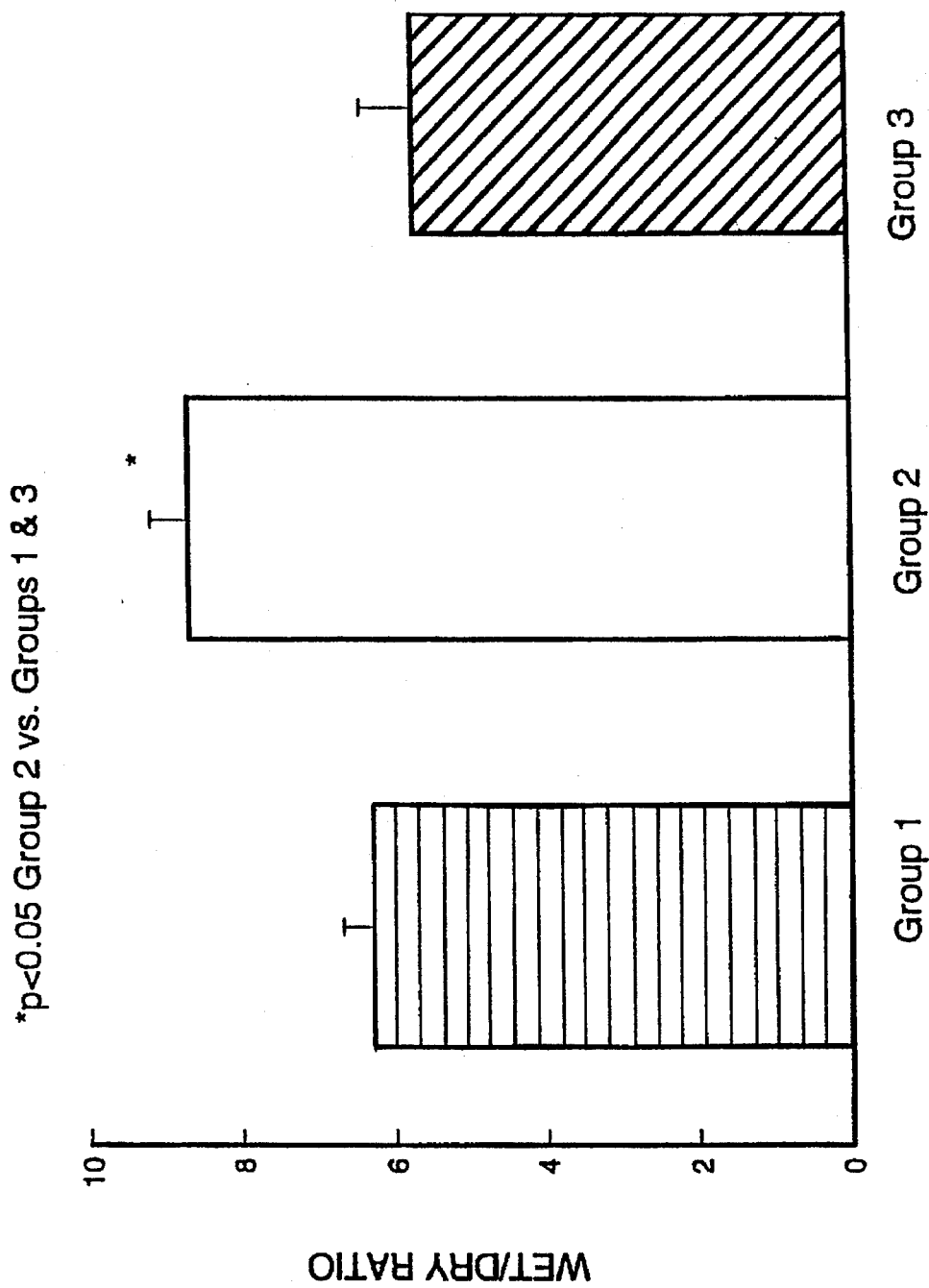

METHOD FOR EMPLOYING THE DELTA OPIOID DADLE TO EXTEND TISSUE SURVIVAL TIME DURING ISCHEMIA

FIELD OF THE INVENTION

During the past thirty years, several methods have been developed for preserving solid organs for transplantation. In almost all cases, such preservation methods have included flushing or perfusing organs with cold crystalloid or plasma solutions. The recent introduction of the University of Wisconsin Solution now permits kidneys to be stored for 72 hours and livers for 24 hours in animal studies. However, safe preservation times for the heart and lungs are still limited to 4 to 6 hours regardless of the solution used (including University of Wisconsin Solution, Collins Solution, Euro-Collins Solution, or these solutions with many additives).

In the last few years, our group found that a delta opioid, DADLE ([D-Ala$^2$, d-Leu$^5$]-Enkephalin), could extend tissue survival time substantially during normothermic multiple organ preservation. Because very few groups in the world use normothermic multiple organ techniques, the use of the DADLE in normothermic preparations is currently still limited.

BACKGROUND OF THE INVENTION

An acute shortage of donor organs greatly limits access to transplantation. As of Jul. 22, 1992, according to the United Network for Organ Sharing (UNOS), 21,120 patients were awaiting a kidney; 2,183 a liver; 783 a pancreas; 2,557 a heart; 166 a heart-lung; and 889 a lung transplant. Since December 1986, the demand for transplantation has increased by 188%, from 9,632 to 27,678 potential recipients. Meanwhile, there has been little change in the supply of organ donors. Between 1986 and 1991, the number of donors has been between 4,000 and 4,500 annually. As a result, the number of patients who die while awaiting a transplant continues to increase: from 1,537 in 1988 to 2,077 in 1990, with variation according to the procedure required.

The paucity of donor organs for human transplantation can be remedied to a certain extent by procuring organs from distant sites, particularly from large urban areas where accident rates are high. Heart and lung transplantations would benefit greatly, as has been the case for renal transplantation, from the development of satisfactory methods of organ preservation to extend the travel time of donor organs.

The criteria for lung donors are very strict; only 10% to 15% of suitable heart donors will also be potential lung donors. With current clinical methods of lung preservation, 4 to 6 hours of storage proves largely successful, and sometimes a period of ischemia of up to 9 hours is tolerated with depressed lung function after transplant. Several investigators have reported preservation for periods ranging from 20 to 48 hours, but none of these reports has been associated with consistent, reliable results, which would be required for clinical application. Methods with such a short preservation time have three primary disadvantages: (1) they limit the geographic area from which grafts can be obtained; (2) they limit the time available for histocompatibility tests; and (3) they increase the likelihood of inadequate organ function after transplantation.

Clinical methods used for lung preservation for transplantation have included immediate implantation (donor transported to the hospital where the recipient is located); hypothermic atelectasis, hypothermic pulmonary artery flushing and storage, with or without varying degrees of inflation; donor core cooling on cardiopulmonary bypass; and autoperfused heart-lung preparation at normothermia.

Single-flush perfusion of the lungs is currently the most widely practiced technique in lung preservation. However, when simple flushing with preservation solution is used, the result is always unsatisfactory. Even with many different additives and modifications to the solution, lung function is severely compromised after more than 12 hours of preservation. For years, numerous chemicals (such as prostaglandins, oxygen free-radical scavengers, platelet activating factor antagonists or leukocyte depletion, corticosteroids, and other chemicals) have been added to pulmonary artery flush solutions such as modified Euro-Collins solution, University of Wisconsin solution, UCLA solution, Stanford solution, and Bretschneider's solution. Although various reports have indicated that these added chemicals provide improved effects, no additive has been proved reliable. Our results from Group 2 (described elsewhere) appear to agree with previous studies. Euro-Collins solution alone is known to cause pulmonary vasoconstriction, and the safe preservation time is usually 4 to 6 hours.

Long-term preservation of donor organs in vitro will also make it possible to treat the donor organ before it is transplanted, thus reducing or possibly eliminating the necessity for immunosuppressive treatment of the recipient.

Our previous study showed that DADLE can effectively extend tissue survival time in a normothermic multiorgan preservation block. Because of technical difficulties, normothermic multiple organ preparations are used by only a few groups around the world; the use of DADLE in such preparations is limited at the present time. However, if DADLE can also extend tissue survival time in hypothermic storage, the potential of adding positive effects to presently used preservation solutions will be tremendous. Not only will this technique improve hypothermic organ preservation, but it will also improve the effectiveness of various currently used cardioplegic solutions and possibly of other hypothermic treatment modalities.

SUMMARY OF THE INVENTION

This invention involves a method for extending the survival time of mammalian lung tissue subjected to ischemia, such as that which occurs during cardioplegia during open-heart surgery and treatment of shock. This method comprises flushing the lung tissue with a preservation solution comprising a therapeutic dose (e.g., 1 to 10 mg/Kg) of the delta opioid DADLE ([D-Ala$^2$, d-Leu$^5$]-Enkephalin) and then preserving the lung in hypothermia. The results obtained have been very encouraging.

Our rat lung preservation study indicated that when DADLE was added to the Euro-Collins solution, the lungs preserved for 24 hours maintained excellent function, a result never achieved by previous reports using Euro-Collins solution alone.

Severe pulmonary edema, hemorrhage, and occlusive pulmonary artery resistance occurred in Group 2 (without DADLE) within 30 minutes of perfusion. Perfusion studies were carried out for more than 60 minutes in Group 1 (Normal) and Group 3 (with DADLE). Pulmonary blood flow was lower in Group 2 than in either Group 1 or Group 3. Pulmonary vascular resistance (PVR) was much higher in Group 2 than in Groups 1 and 3 (p<0.05, FIG. 1). Airway pressure and airway resistance (AWR) were much higher in Group 2 than in Group 1 and Group 3 ($p<0.05$). AWR was also higher in Group 3 than in Group 1 after 20 minutes of perfusion ($p<0.05$, FIG. 2). Oxygen tensions from the pulmonary vein ($pvO_2$) of the isolated lung in Group 2 were lower than those in Group 1 and Group 3 ($p<0.05$, FIG. 3). Alveolar-arterial oxygen difference was much higher in Group 2 than in Group 1 and Group 3 ($p<0.05$, FIG. 4). Lung tissue wet/dry weight ratio after perfusion was much higher in Group 2 than in Group 1 and Group 3 (FIG. 5). The most interesting finding is the near-normal tissue wet/dryweight ratio, pulmonary blood flow, pulmonary vascular resistance, and oxygen transporting capacity of the lungs after 24-hour preservation in the group using DADLE. In comparison with normal lungs (without preservation), airway resistance in the lungs preserved with DADLE increased slightly after preservation. However, this resistance was much lower than that of the lungs preserved with Euro-Collins solution alone.

The results clearly demonstrate, for the first time, that DADLE can effectively enhance hypothermic lung preservation in rats.

The mechanism by which DADLE extends tissue survival time is not at all clear. Because of the complexity of opioids and their receptors, studies to date have primarily concentrated on the reactions of different opioids with different receptors. Studies of the effects of opioids on the cardiovascular system have been performed for years, but the results are very controversial. Through a Medline search, we have found no reports relating opioid agonists to tissue metabolism or organ preservation other than those we ourselves have published. Delta opioid receptors may be responsible for naturally occurring animal hibernation, because continuous subcutaneous administration of naloxone, an opioid antagonist, diminished the frequency and length of hibernation bouts in ground squirrels. This indicates that animal hibernation may be induced by a mechanism involving an endogenous opioid that acts through binding to receptor sites.

We can only speculate about possible mechanisms by which DADLE extends tissue survival time during hypothermia. The effect may be related either to the inhibitory effect of DADLE on tissue metabolism, or to the ability of DADLE to protect tissue from various types of damage during ischemia. The results of our study indicated that the improved preservation may also be related to the effect of DADLE on vasodilation, as shown by low vascular resistance after preservation. This supposition is also supported by our previous experiment, in which severe reduction of arterial blood pressure occurred after intravenous injection of DADLE into anesthetized animals.

BRIEF DESCRIPTION OF THE DRAWINGS

FIG. 4. Comparison of alveolar-arterial oxygen difference in the three groups of rat lungs (lower is better).

FIG. 5. Lung tissue wet/dryweight ratios after preservation and perfusion in the same three groups (lower is better).

DETAILED DESCRIPTION OF THE INVENTION

METHODS

Figure 1:
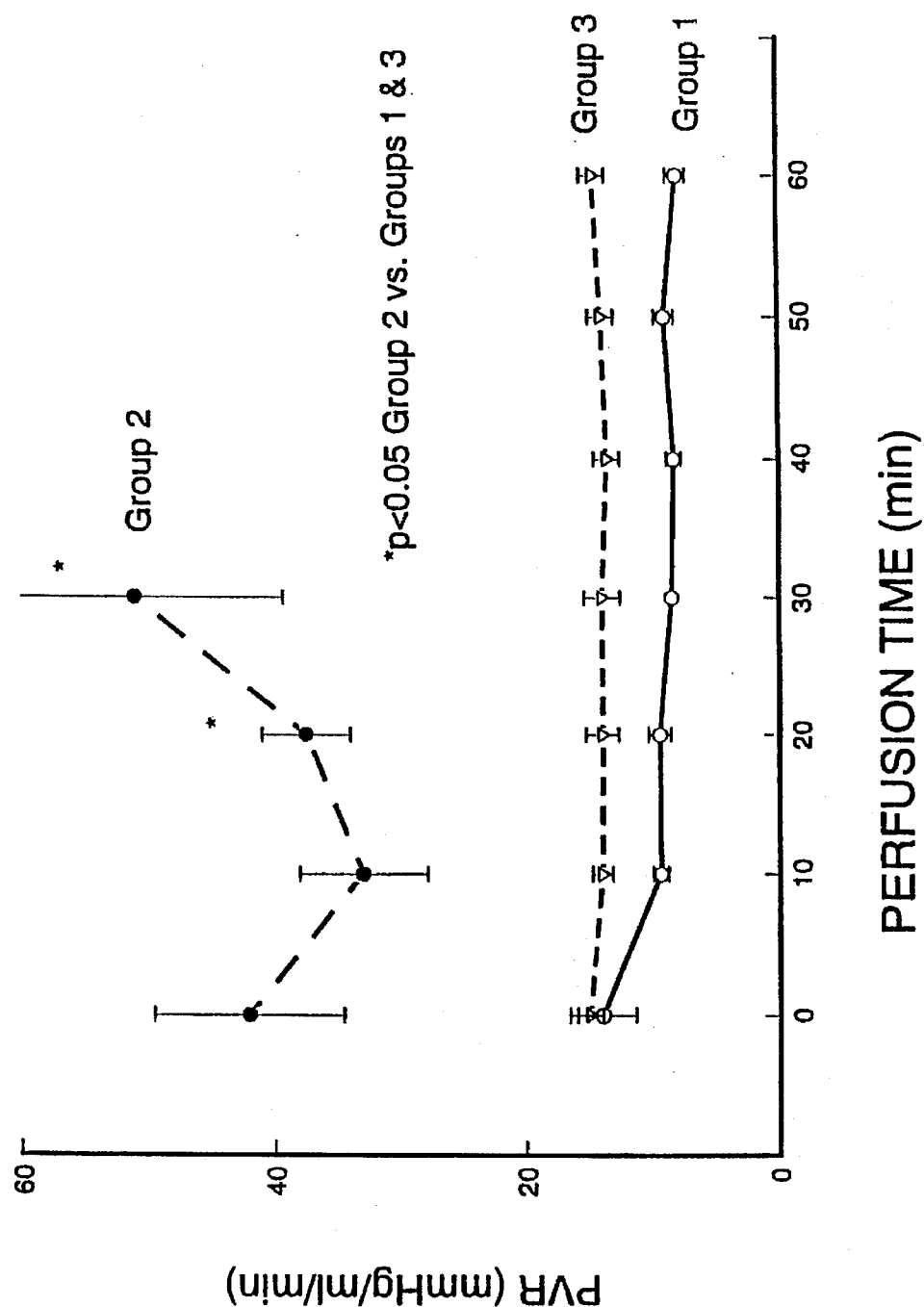
FIG. 1. Comparison of pulmonary vascular resistance (PVR) in three groups of rat lungs (the lower the better).

Healthy adult rats (250 to 300 gm) were allowed free access to food and water before surgery. All animals received humane care in compliance with the "Principles of Laboratory Animal Care" formulated by the National Society for Medical Research and the "Guide for the Care and Use of Laboratory Animals" prepared by the Institute of Laboratory Animal Resources and published by the National Institutes of Health (NIH publication No. 86–23, revised 1985).

Preparation of hypothermic isolated lung storage:

The rats were anesthetized by intraperitoneal injection of sodium pentobarbital (35 to 50 mg/kg wt). The cervical trachea was cannulated, and each animal was ventilated by a rodent respirator using room air. Tidal volume of 2.5 to 3.5 ml and rate of 40 to 50 rpm were maintained. The retrosternal space was exposed by blunt dissection, and two large straight clamps were applied in a parallel fashion across the sternum. Care was taken not to injure the lungs and vessels beneath. The thorax was opened by median sternotomy. After administration of 300 IU heparin iv, the inferior pulmonary ligaments were carefully divided. The left superior vena cava was dissected, ligated, and divided. The hilum of the left lung was approached anteriorly, and the vessels and bronchus were separated by blunt dissection. The left pulmonary artery was dissected, and a suture was placed around it. The main pulmonary artery was transected through the transverse sinus, and a cannula was placed in the left pulmonary artery through the transected main pulmonary artery. The suture around the left pulmonary artery was tied, and the left atrium was partly excised to decompress the left atrium. The left lung was flushed with cold preservation solution, removed, and preserved at 4° C. for 24 hours before functional studies. This simulates removing a lung from a donor, said lung being preserved before being transplanted into a second individual needing a new lung.

Technique of isolated lung function studies.

A perfusion apparatus consisting of a living host rat and a temperature-controlled, humidified chamber was used for isolated lung function studies. The host rat was anesthetized by intraperitoneal injection of sodium pentobarbital (35–50 mg/kg wt). The cervical trachea was cannulated, and the animal was ventilated by a rodent respirator using room air. Tidal volume of 2.5 to 3.5 ml and rate of 40 to 50 rpm were used. The right internal jugular vein was cannulated with a 2-mm catheter. Heparin sodium 3 mg/kg was infused intravenously, and both carotid arteries were cannulated with 0.5-mm catheters. The catheter in the right carotid artery was connected to a Gould pressure transducer for arterial blood pressure monitoring. Blood from the host rat was withdrawn by gravity from the right internal jugular vein to the pulmonary artery of the isolated lung. The isolated lung was perfused with host venous blood by using a hydrostatic pressure of 25 mmHg. The isolated lung was suspended in a perfusion chamber, which was immersed in a 37° C. water bath. Blood returned from the isolated lung was collected in the perfusion chamber. A roller pump returned the blood from the perfusion chamber to the left carotid artery of the host rat. The rate of blood returning from the chamber was adjusted to maintain satisfactory systemic pressure.

During the perfusion period, the isolated lung was ventilated with room air at respiratory rate of 40 to 50 rpm, tidal volume of 2.5 ml, and PEEP of 0.5 cm $H_2O$. Such ventilation and perfusion may, for example, be applied to an isolated lung wherein ischemia occurs during cardioplegia during open-heart surgery and treatment of shock.

After an initial 5- to 10-minute equilibration period, blood samples from the pulmonary artery and vein were taken every 10 minutes for blood gas analysis. Perfusion pressure, perfusion flow, airway pressure, and tidal volume were recorded. Through the use of these parameters, pulmonary vascular resistance and airway resistance were calculated. At the end of the experiment, lung tissue samples were taken for wet/dry weight ratio measurements.

Experimental Results

Animal groups studied

Twenty-four rats were used in this study. The rats were divided into three groups. Group 1 (N=8) was used as normal controls, in which the left lung was removed and immediately transferred to the perfusion apparatus for function studies. In this group, no interruption of ventilation occurred, and interruption of lung blood perfusion was routinely less than 10 to 20 seconds. Lung function in this group was assumed to be normal. In Group 2 (N=8), the left lung was flushed with 10 to 15 ml of 4° C. Euro-Collins solution at a gravity gradient of 20 cm $H_2O$ and immersed in 4° C. Euro-Collins solution for 24 hours. In Group 3 (N=8), the left lung was also flushed with 10 to 15 ml of 4° C. Euro-Collins solution, followed by 3 to 5 ml of 4° C. DADLE solution (1 mg/Kg, Peninsula Lab, Belmont, Calif.), and then immersed in 4° C. Euro-Collins solution for 24 hours. In Groups 2 and 3, the bronchus was clamped at the end of inspiration to keep the lung inflated during storage.

Statistical analysis.

Two-way analysis of variance (ANOVA) was used for repeated measurements. If significance was established, the Student-Newman-Keuls test was used to analyze the difference between individual groups. A value of $p<0.05$ was considered significant. All results were expressed as means±SEM.

Overall performance.

Severe pulmonary edema and hemorrhage occurred in Group 2 (Euro-Collins solution only) within 30 minutes of perfusion, and no preparation could be perfused for more than 30 minutes. This phenomenon did not occur in either Group 1 (normal) or Group 3 (Euro-Collins plus DADLE), and perfusion studies could be carried out for more than 60 minutes in these two groups. Oxygen tension and carbon dioxide tension in the pulmonary artery and vein of the isolated lung during the 60-minute reperfusion period remained stable and were very comparable between Group 1 and Group 3. Pulmonary vascular resistance and airway resistance were also stable during the perfusion period in these two groups.

Blood flow and pulmonary vascular resistance (PVR) of the isolated lung.

Pulmonary blood flow ranged from 1.91±0.27 to 3.31±0.53 ml/min in Group 1; 0.61±0.10 to 0.82±0.10 ml/min in Group 2; and 1.68±0.09 to 1.94±0.21 ml/min in Group 3. Pulmonary blood flow was lower in Group 2 than in Group 1 and Group 3. In Group 1, PVR ranged from 7.5±0.8 to 14±2.6 mmHg/ml/min. In Group 2, it ranged from 36±5 to 54±11 mmHg/ml/min; and in Group 3, it ranged from 13.6±1 to 15±1 mmHg/ml/min. Because of very high pulmonary vascular resistance in Group 2 ($p<0.05$ as compared to Group 1 and Group 3), perfusion could not be continued after 30 minutes, indicating severe tissue edema in this group. No significant difference was found in pulmonary vascular resistance between Group 1 and Group 3 (FIG. 1).

Airway pressure and resistance (AWR) of the isolated lung.

When a tidal volume of 2.5 ml was used, airway pressure ranged from 6.4±0.3 to 9.6±1.2 mmHg in Group 1; 13.9±0.9 to 18.4±1.1 mmHg in Group 2; and 9.5±1.1 to 13.3±1.2 mm Hg in Group 3. Airway pressure was much higher in Group 2 ($p<0.05$ as compared to Group 1 and Group 3). It was also higher in Group 3 than in Group 1.

Figure 2:
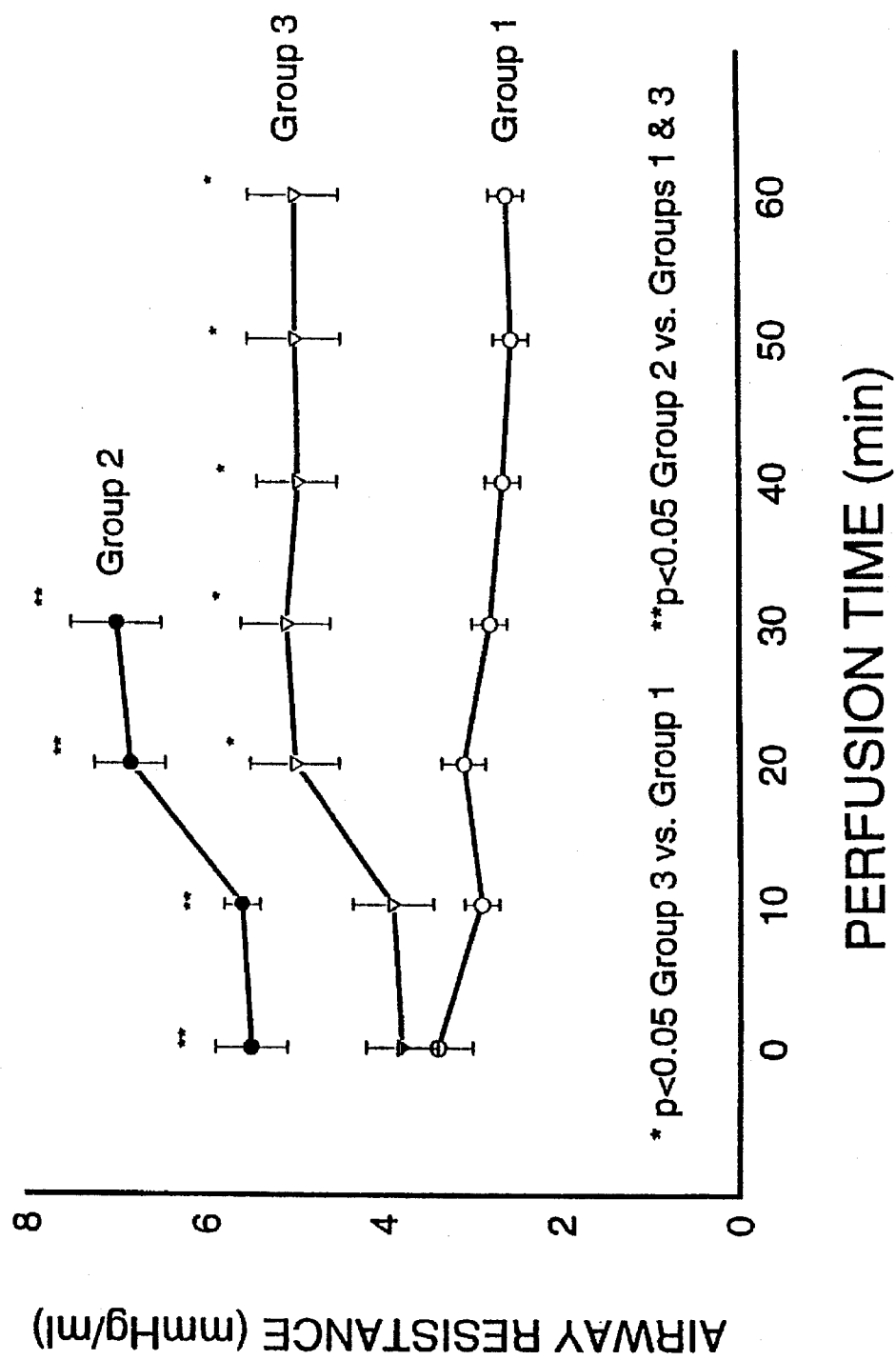
FIG. 2. Comparison of airway resistance in the same three groups of rat lungs (lower is better).

AWR in Group 1 ranged from 2.6±0.2 to 3.7±0.5 mmHg/ml. It ranged from 5.5±0.3 to 7±0.4 mmHg/ml in Group 2 and from 3.7±0.3 to 5.0±0.5 mmHg/ml in Group 3. AWR was much higher in Group 2 than in Groups 1 and 3 ($p<0.05$). However, AWR was also higher in Group 3 than in Group 1 after 20 minutes of perfusion ($p<0.05$, FIG. 2).

Blood gases in the inflow and outflow of the isolated lung.

Figure 3:
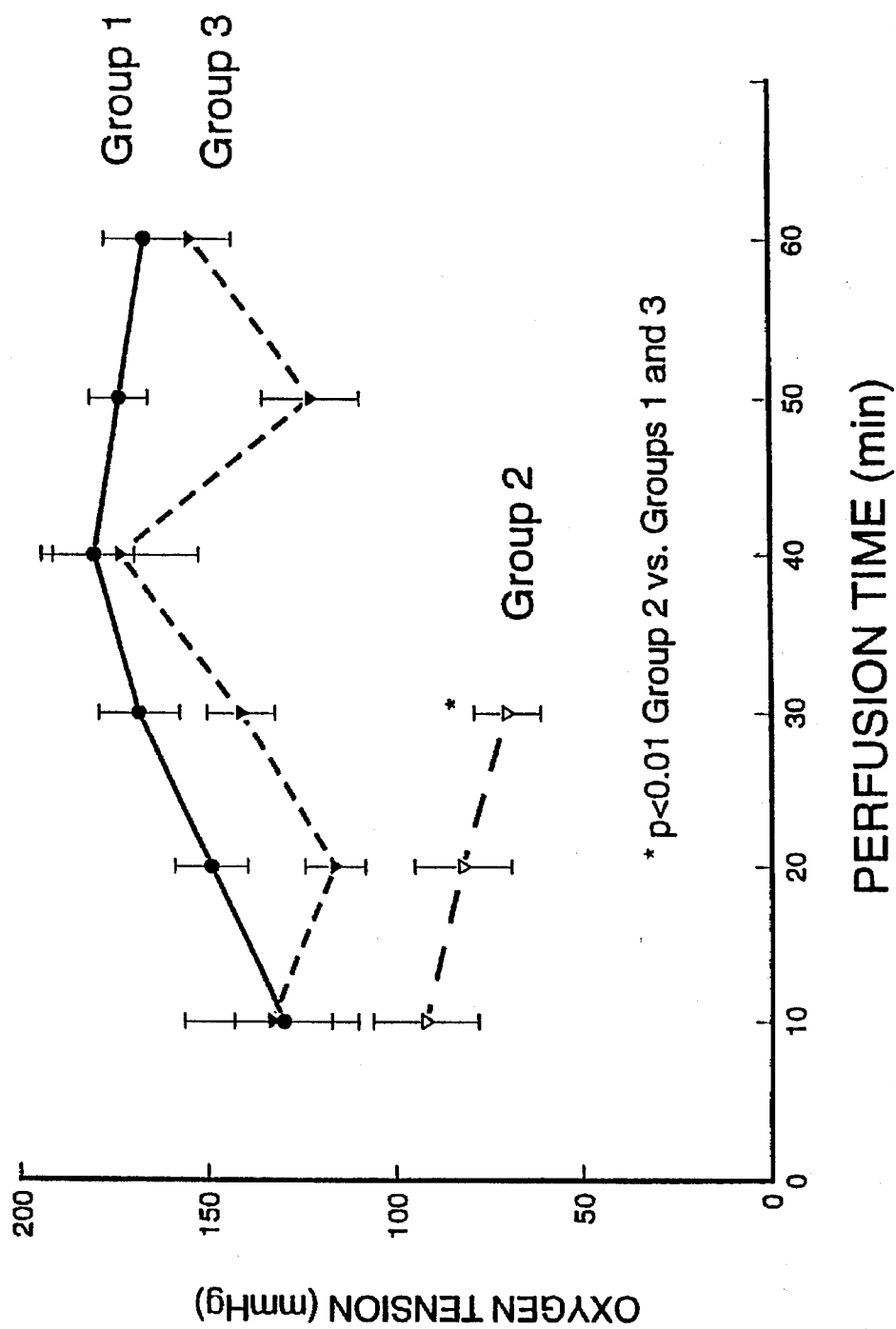
FIG. 3. Comparison of oxygen tensions in the isolated pulmonary vein in the three groups of rat lungs (higher is better).

Mean oxygen tensions in the pulmonary artery (before oxygenation) were 33±1.6 to 36±2.1 for Group 1; 48±5 to 52±7 for Group 2; and 53±4.0 to 60±3.7 for Group 3. Mean oxygen tensions from the pulmonary vein (after oxygenation by the isolated lung) were 130±13 to 180±11 mmHg for Group 1; 70±9.0 to 92±14 in Group 2; and 116±8.0 to 173±21 in Group 3. Oxygen tensions in Group 2 were lower than in Group 1 and Group 3 during perfusion and became worse when perfusion time was longer, indicating impaired oxygenation capacity in Group 2 (FIG. 3). Carbon dioxide tensions in the pulmonary artery (before the blood was oxygenated by the isolated lung) were 30±2.7 to 38±2 in Group 1; 41±4 to 41±7 in Group 2; and 16±2 to 23±3 in Group 3. Carbon dioxide tensions in the pulmonary vein (after the blood was oxygenated by the isolated lung) were 17±0.6 to 19±2.0 in Group 1; 17±2.5 to 23±4 in Group 2; and 16±2 to 23±3 in Group 3. No statistically significant difference was found among the three groups, although perfusion time was much shorter in Group 2.

Alveolar-arterial oxygen difference:

Alveolar-arterial oxygen difference (A-a$O_2$ difference) ranged from 4.68±4.62 to 30.29±10.28 mmHg in Group 1. It ranged from 44.01±10.94 to 54.88±6.16 mmHg in Group 2, and from 0.46±0.46 to 23.49±5.45 mmHg in Group 3. A-a$O_2$ difference was much higher in Group 2 than in either Group 1 or Group 3 ($p<0.05$, FIG. 4).

Lung tissue wet/dry weight ratio after perfusion.

Lung tissue wet/dry weight ratio after perfusion was 6.3±0.4 in Group 1. It was 8.7±0.5 in Group 2 and 5.7±0.7 in Group 3. Tissue wet/dry weight ratio was much higher in Group 2 than in Group 1 and Group 3 ($p=0.005$), even though the perfusion time was only 30 minutes in Group 2. There was no difference in tissue wet/dry weight ratio between Group 1 and Group 3. See FIG. 5.

In summary, the present invention clearly demonstrates that DADLE has a very positive effect on hypothermic rat lung preservation. On the basis of the described experimental work and other published and unpublished observations involving representative animals (i.e., rodents and canines), the conclusions reached herein are believed generally applicable to mammals as a group. The mechanism of this effect is not clear and deserves further study.

Composition of several preservation solutions

Collins M solution

| | |
|---|---|
| Potassium | 115 mmol/L |
| Sodium | 10 mmol/L |
| Chloride | 15 mmol/L |
| Phosphate | 13 mmol/L |
| Bicarbonate | 10 mmol/L |
| Magnesium | 3 mmol/L |
| Glucose | 139 mmol/L |

Euro-Collins solution

| | |
|---|---|
| Sodium | 10 mmol/L |
| Potassium | 115 mmol/L |
| Chloride | 15 mmol/L |
| Bicarbonate | 10 mmol/L |
| Phosphate | 58 mmol/L |
| Glucose | 38.5 g/L |

University of Wisconsin solution

| | |
|---|---|
| Sodium | 27 mmol/L |
| Potassium | 115 mmol/L |
| Chloride | 0 mmol/L |
| Phosphate | 25 mmol/L |
| Magnesium | 5 mmol/L |
| Raffinose | 30 mmol/L |
| Lactobionate | 100 mmol/L |
| Adenosine | 1.3 g/L |
| Glutathione | 0.9 g/l |
| Allopurinol | 0.1 g/l |
| Hydroxyethyl starch | 50 g/l |

I claim:

1. A method for extending the survival time of at least one isolated mammalian lung subjected to ischemia and hypothermia, wherein said lung is treated during a period of perfusion with a preservation solution comprising a preservation effective amount of the delta opioid DADLE ((D-Ala$^2$, D-Leu$^5$)-Enkephalin) at a hypothermic temperature.

2. The method of claim 1 wherein the amount of DADLE in the preservation solution is within the range of 1 to 10 mg/Kg.

3. The method of claim 1 wherein the hypothermic conditions include the temperature being maintained at 4° C.

4. The method of claim 2 wherein the hypothermic conditions involve the temperature being maintained at 4° C.

5. The method of claim 4 wherein the lung is effectively preserved for at least 24 hours without the loss of function.

6. The method of claim 1 wherein the preservation solution is Euro-Collins solution.

7. The method of claim 1 wherein the lung has been removed from a donor and is being preserved before being transplanted into a second individual needing a new lung.

8. The method of claim 1 wherein the ischemia occurs during cardioplegia during open-heart surgery and treatment of shock.

9. The method of claim 8 wherein the isolated lung is also ventilated during the perfusion period.

* * * * *